United States Patent
Bjurbo et al.

(10) Patent No.: US 12,036,063 B2
(45) Date of Patent: Jul. 16, 2024

(54) AIRWAY DETECTION USING ACOUSTIC SIGNALS

(71) Applicant: Avent, Inc., Alpharetta, GA (US)

(72) Inventors: Karl Thomas Bjurbo, Cumming, GA (US); James F. Tassitano, Marietta, GA (US); Hilton M. Kaplan, New York, NY (US); Don J. McMichael, Roswell, GA (US)

(73) Assignee: Avent, Inc., Alpharetta, GA (US)

( * ) Notice: Subject to any disclaimer, the term of this patent is extended or adjusted under 35 U.S.C. 154(b) by 477 days.

(21) Appl. No.: 16/944,666

(22) Filed: Jul. 31, 2020

(65) Prior Publication Data

US 2022/0031278 A1    Feb. 3, 2022

(51) Int. Cl.
| A61B 7/00 | (2006.01) |
| A61B 5/00 | (2006.01) |
| A61B 7/02 | (2006.01) |
| G10L 21/14 | (2013.01) |
| G10L 25/51 | (2013.01) |

(Continued)

(52) U.S. Cl.
CPC ............ *A61B 7/008* (2013.01); *A61B 5/0002* (2013.01); *A61B 5/743* (2013.01); *A61B 7/023* (2013.01); *G10L 21/14* (2013.01); *G10L 25/51* (2013.01); *H04R 1/028* (2013.01); *H04R 1/083* (2013.01);

(Continued)

(58) Field of Classification Search
CPC ....... A61B 7/008; A61B 5/0002; A61B 5/743; A61B 7/023; A61B 2562/0204; A61B 5/061; A61B 8/12; A61B 8/445; A61B 8/4488; A61B 18/149; A61B 34/76; G10L 21/14; G10L 25/51; H04R 1/028; H04R 1/083; H04R 1/46; A61M 16/0488;

(Continued)

(56) References Cited

U.S. PATENT DOCUMENTS

| 5,785,051 A | 7/1998 | Lipscher et al. |
| 5,967,984 A * | 10/1999 | Chu .................. A61B 8/445 |
| | | 607/122 |

(Continued)

FOREIGN PATENT DOCUMENTS

| WO | WO 2016/200334 A1 | 12/2016 |
| WO | WO 2019/186589 A1 | 10/2019 |
| WO | WO 2020/044758 A1 | 3/2020 |

*Primary Examiner* — Patrick Fernandes
(74) *Attorney, Agent, or Firm* — Dority & Manning, P.A.

(57) ABSTRACT

A tubing assembly for electronic catheter guidance systems is provided and can include a catheter, an internal acoustic transducer and an external acoustic transducer. The catheter extends in a longitudinal direction and has proximal and distal ends that define a lumen therebetween. Further, the catheter is configured for placement within a patient's digestive or respiratory tract. The internal acoustic transducer can be located within the catheter's lumen, and the external acoustic transducer can be located on or outside the patient's body. The transducers can transmit and/or receive acoustic signals as directed by a processor and communicate with the processor to deliver sound data to a display device. The frequency response and/or attenuation of the signals can indicate placement of the catheter in the digestive tract compared to the respiratory tract. A catheter guidance system and method for accurately placing a catheter in the digestive or respiratory tract are also provided.

11 Claims, 9 Drawing Sheets

(51) Int. Cl.
  *H04R 1/02* (2006.01)
  *H04R 1/08* (2006.01)
  *H04R 1/46* (2006.01)

(52) U.S. Cl.
  CPC ........ *H04R 1/46* (2013.01); *A61B 2562/0204* (2013.01)

(58) Field of Classification Search
  CPC ...... A61M 2205/3375; A61M 16/0411; A61M 16/0057
  See application file for complete search history.

(56) References Cited

U.S. PATENT DOCUMENTS

| | | | |
|---|---|---|---|
| 6,349,720 B1 | 2/2002 | Clark | |
| 6,705,319 B1* | 3/2004 | Wodicka | A61M 16/0488 128/207.14 |
| 6,913,259 B2 | 7/2005 | Phinney et al. | |
| 6,918,391 B1 | 7/2005 | Moore | |
| 7,603,159 B2 | 10/2009 | Rasche | |
| 7,996,059 B2 | 8/2011 | Porath et al. | |
| 8,038,629 B2 | 10/2011 | Solanki et al. | |
| 8,394,031 B2 | 3/2013 | Mansy et al. | |
| 8,617,152 B2 | 12/2013 | Werneth et al. | |
| 8,834,370 B2 | 9/2014 | Evert et al. | |
| 8,923,949 B2 | 12/2014 | Amit et al. | |
| 9,004,069 B2 | 4/2015 | Efrati et al. | |
| 9,031,638 B2 | 5/2015 | Su | |
| 9,486,595 B2 | 11/2016 | Borrye et al. | |
| 9,700,693 B2 | 7/2017 | Qiu | |
| 9,707,363 B2 | 7/2017 | Mansfield et al. | |
| 9,861,776 B2 | 1/2018 | Lin et al. | |
| 10,206,607 B2 | 2/2019 | Prough et al. | |
| 10,219,777 B2 | 3/2019 | Freeman et al. | |
| 10,226,608 B2 | 3/2019 | Imran | |
| 10,383,646 B2 | 8/2019 | Baker et al. | |
| 10,478,072 B2 | 11/2019 | Tearney et al. | |
| 2002/0151789 A1* | 10/2002 | Mansy | A61B 8/08 600/431 |
| 2003/0034035 A1 | 2/2003 | Raphael | |
| 2006/0081255 A1 | 4/2006 | Miller et al. | |
| 2007/0167825 A1* | 7/2007 | Lee | A61B 8/4461 600/463 |
| 2013/0158537 A1 | 6/2013 | Deladi et al. | |
| 2013/0274712 A1* | 10/2013 | Schecter | A61B 34/76 604/100.01 |
| 2015/0087922 A1* | 3/2015 | Bardy | G16H 40/67 600/301 |
| 2016/0022943 A1 | 1/2016 | Kanowitz | |
| 2016/0279366 A1 | 9/2016 | Mansfield et al. | |
| 2017/0128039 A1 | 5/2017 | Waldstreicher et al. | |
| 2017/0340522 A1 | 11/2017 | Mansfield et al. | |
| 2018/0078195 A1* | 3/2018 | Sutaria | A61B 5/1073 |
| 2018/0168540 A1 | 6/2018 | Van Bruggen et al. | |
| 2019/0030312 A1 | 1/2019 | Davis et al. | |
| 2019/0340837 A1 | 11/2019 | Shmayahu et al. | |

\* cited by examiner

AIRWAY DETECTION USING ACOUSTIC SIGNALS

FIELD OF THE INVENTION

The subject matter of the present invention relates generally to a system and method for placement of a medical device through the esophagus, as distinguished from the airway, using sound waves to detect the location of the medical device within these structures of the patient's anatomy.

BACKGROUND

Physicians and other health care providers frequently use catheters to treat patients. The known catheters include a tube which is inserted into the human body. Certain catheters are inserted through the patient's nose or mouth for treating the gastrointestinal tract. These catheters, sometimes known as enteral catheters, typically include feeding tubes. The feeding tube lies in the stomach or intestines, and a feeding bag delivers liquid nutrient, liquid medicine or a combination of the two to the patient; or the feeding tube can be used to aspirate gastrointestinal contents if needed.

When using these known enteral catheters, it is important to place the catheter along an appropriate route, and so that the end of the catheter is left at the proper location within the human body. Erroneous placement of the catheter tip may injure or harm the patient. For example, if the health care provider erroneously places an enteral catheter into the patient's trachea, lungs, or other regions of the respiratory system rather than through the esophagus and to the stomach and/or intestines (to reach the desired location in the digestive tract for delivering nutrients or medicine, or for aspirating gastrointestinal contents), liquid may be introduced into the lungs with harmful, and even fatal, consequences. In particular, the entrance to the esophagus of the digestive tract and to the trachea of the respiratory system are in close proximity to each other and are traditionally "blind" to the health care provider during feeding catheter placement, which creates a dangerous risk for erroneous catheter placement.

In some cases, health care providers use X-ray machines to gather information about the location of catheters within the body. There are several disadvantages with using X-ray machines. For example, these machines are relatively large and heavy, expose the patient to a relatively high degree of X-ray radiation, and consume a relatively large amount of energy. Also, these machines are typically not readily accessible for use because, due to their size, they are usually installed in a special X-ray room; and due to their weight and bulk are difficult to move around. This room can be far away from the patient's room. Therefore, health care providers can find it inconvenient to use these machines for performing catheter insertion procedures. Moreover, even X-rays may not be conclusive as to the location of the catheter tip, as the natural and continuous movement of the internal organs can make it difficult for the physician interpreting the X-ray to be sure of the actual location of the distal end of the catheter in some cases. In addition, using X-ray technology is expensive and is a time-consuming task that can create unnecessary delays in delivering critical nutrients to the patient. These delays become particularly clinically significant in premature infants and neonates who may not be able to be sustained for the hours that getting an X-ray performed and read can take, before being fed.

Another existing catheter locating means involves using an electromagnetic coil positioned inside the catheter and an electromagnetic coil locating receiver outside of the patient's body. The electromagnetic coil is generally incorporated into a stylet or guide wire which is inserted within the catheter or may be incorporated into the catheter itself. The coil locating receiver can be used to determine the distance the coil is from the receiver and its depth in the patient's body; can track both of these in real-time; and can communicate with a display to show a reference image of a non-subject body and an image of the coil located on the display with the reference image and its movement over time. However, these systems also have several disadvantages when used without additional catheter placement confirmation. For example, the coil locating receiver is a large device that must rest in a precise location and orientation outside the patient's body and does not permit for adjustments due to each individual patient's anatomical size or shape. However, a patient undergoing a feeding tube placement will be agitated and sudden movements are expected, which can move the coil locating receiver, thus increasing the likelihood of positional errors or complications in locating the catheter. Additionally, these existing systems can only display the coil location over a reference image of a non-subject (i.e., a generic patient) body without reference to the individual patient's particular anatomy. Thus, these existing systems can only generate generic warnings or alerts when a deviation from an intended path within the body is estimated. Such generic warnings or alerts may be ignored by a health care provider because they provide little specific, actual information regarding the absolute position of the catheter and may not adequately capture a health care provider's attention. Therefore, health care providers can estimate the positioning of the catheter using the electromagnetic coil and coil locating receiver but cannot readily tell if the catheter is passing through the patient's esophagus as intended, or instead through the trachea which overlies the esophagus in a frontal plane and so can confound the decision.

Consequently, there is a need for a system for notifying a user of the positioning of a medical device within a patient's body in real-time to ensure more accurate catheter placement. In particular, a notification system that is easy to use and provides a clear deviation alert when the medical device is improperly positioned would also be useful.

SUMMARY

Objects and advantages of the invention will be set forth in part in the following description, or may be obvious from the description, or may be learned through practice of the invention.

According to one particular embodiment, a tubing assembly is provided. The tubing assembly includes a catheter having a proximal end and a distal end and extending in a longitudinal direction, wherein the proximal end and the distal end define a lumen therebetween, and wherein the catheter is configured for placement within a digestive tract of a patient; and an internal acoustic transducer.

In one embodiment, the internal acoustic transducer can be located within the lumen of the catheter. Further, the internal acoustic transducer is located at the distal end of the catheter.

In another embodiment, the internal acoustic transducer can be configured to receive or transmit sound data as controlled by a processor in real-time. Further, the internal acoustic transducer is configured for a wired connection or a wireless connection to the processor.

In still another embodiment, the internal acoustic transducer can be protected from fluid ingress by a flexible coating.

In yet another embodiment, the acoustic transmitter can be contained within a microphone.

In another embodiment, the tubing assembly can include an attachment including an external acoustic transducer.

According to another particular embodiment of the present invention, a catheter guidance system is provided. The system includes (a) a processor; (b) a power source; (c) a display device; (d) an external acoustic transducer; and (e) a tubing assembly that includes: a catheter having a proximal end and a distal end and extending in a longitudinal direction, wherein the proximal end and the distal end define a lumen therebetween; and an internal acoustic transducer; wherein the internal acoustic transducer receives or transmits sound waves as controlled by the processor in real-time via an electrical connection; wherein the external acoustic transducer transmits or receives the sound waves, further wherein the internal acoustic transducer or the external acoustic transducer communicates acquired sound data to the processor in real-time via an electrical connection; wherein the display device is coupled to the processor and displays a graph of the sound data communicated by the internal acoustic transducer or the external acoustic transducer; and wherein the catheter guidance system alerts a user as to placement of the catheter in a digestive tract of a patient or alerts the user as to placement of the catheter in a respiratory tract of the patient.

In one embodiment, the system can include a memory device storing instructions which, when executed by the processor, cause the processor to (i) interpret the sound data communicated by the internal acoustic transducer or the external acoustic transducer and (ii) cause the catheter guidance system to alert the user as to placement of the catheter in the digestive tract of the patient or alert the user as to placement of the catheter in the respiratory tract of the patient based on the interpretation of the sound data.

In still another embodiment, the internal acoustic transducer can be located within the lumen of the catheter at the distal end of the catheter.

In yet another embodiment, the internal acoustic transducer can be protected from fluid ingress by a flexible coating.

In one more embodiment, the internal acoustic transducer can be contained within a microphone.

In an additional embodiment, the external acoustic transducer can be configured to be placed on or adjacent to the patient's throat or chest.

In another embodiment, the external acoustic transducer can be contained within a speaker.

According to one more particular embodiment of the present invention, a method for determining if a catheter is placed within a digestive tract of a body of a patient is provided. The method includes: (a) inserting a distal end of a tubing assembly into an orifice of the body, wherein the tubing assembly comprises: the catheter, wherein the catheter has a proximal end and a distal end and extends in a longitudinal direction, wherein the proximal end and the distal end define a lumen therebetween; and an internal acoustic transducer; (b) electrically connecting the internal acoustic transducer to a processor via a wired connection or a wireless connection; (c) placing an external acoustic transducer on or adjacent to the patient's throat or chest, wherein the external acoustic transducer is electrically connected to the processor via a wired connection or a wireless connection; (d) activating the internal acoustic transducer, wherein the internal acoustic transducer either receives or transmits sound waves as controlled by the processor in real-time via an electrical connection; (e) advancing the distal end of the catheter inside the body in a direction away from the orifice while the external acoustic transducer is activated; (f) activating the external acoustic transducer to either transmit or receive the sound waves, wherein the internal acoustic transducer or the external acoustic transducer acquire sound data from the sound waves and communicate the sound data to the processor in real-time; and (g) observing a graph of the sound data on a display device coupled to the processor, wherein the display device alerts a user as to placement of the catheter in the digestive tract of the patient or alerts the user as to incorrect placement of the catheter in a respiratory tract of the patient.

In one embodiment, a memory device can store instructions which, when executed by the processor, cause the processor to (i) interpret the sound data communicated by the internal acoustic transducer or the external acoustic transducer and (ii) cause the display device to communicate whether or not the catheter is placed within the digestive tract of the patient based on the interpretation of the sound data.

In another embodiment, the orifice can be a nose or a mouth.

In still another embodiment, the internal acoustic transducer can be located within the lumen of the catheter or within a sampling chamber.

In yet another embodiment, the internal acoustic transducer can be contained within a microphone, and the internal acoustic transducer can be protected from fluid ingress by a flexible coating.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
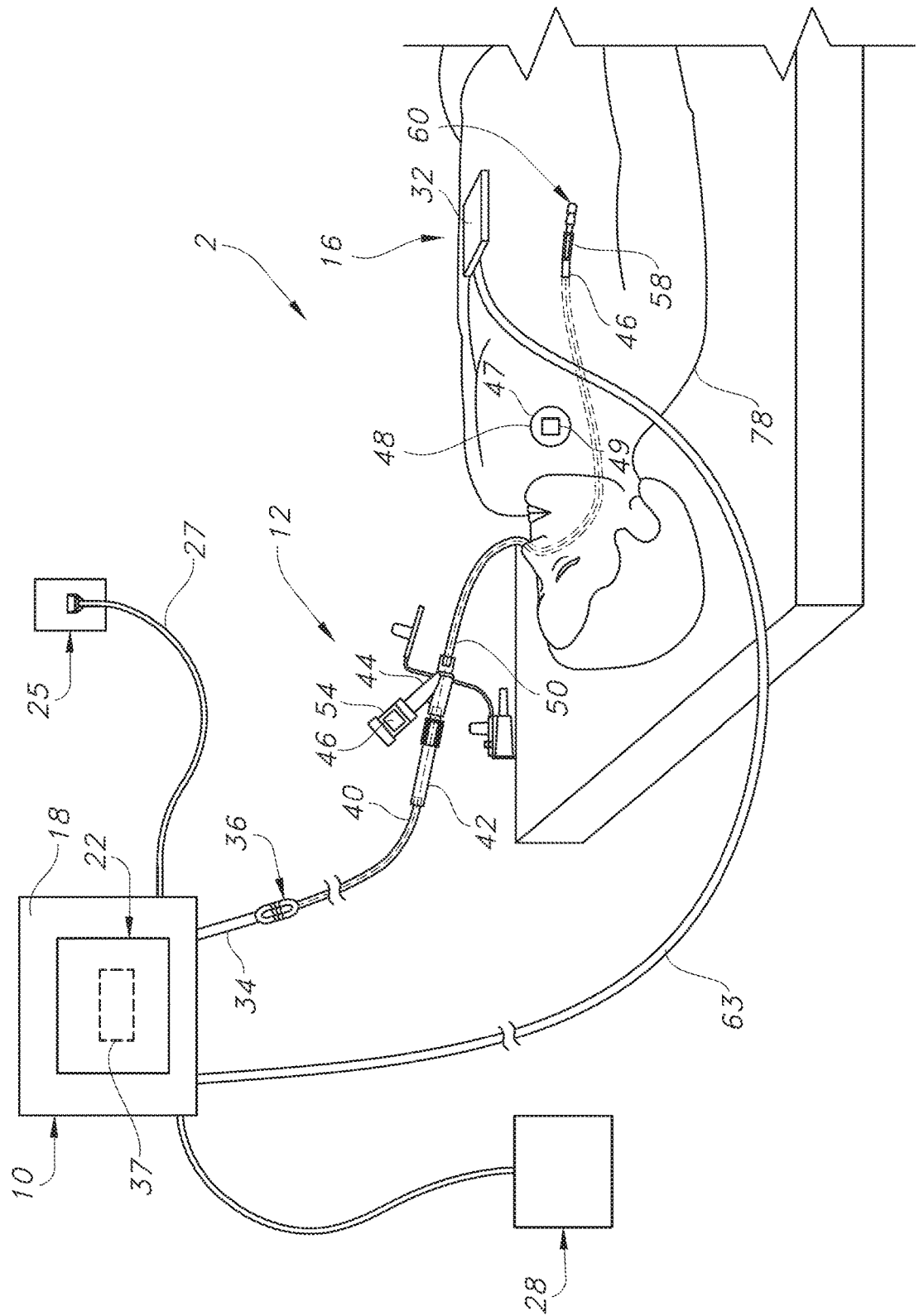
FIG. 1 is a perspective view of the catheter guidance system of the present invention as it is being used to position a catheter within a patient in one embodiment of the present invention, illustrating the display device; electronic catheter unit; internal acoustic transducer that is at least temporarily contained within, or is part of, the electronic catheter unit; and the external acoustic transducer.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a tubing assembly that includes a catheter having a proximal end and a distal end and extending in a longitudinal direction, where the proximal end and the distal end define a lumen therebetween. Further, the catheter can be configured for placement within a digestive tract of a patient. The tubing assembly also includes an acoustic transducer. The acoustic transducer can be located within the lumen of the catheter. The acoustic transducer can be used in conjunction with an additional acoustic transducer located on or outside the patient's body. The acoustic transducer can receive acoustic signals from the external acoustic transducer as directed by a processor, and one or both of the internal acoustic transducer or the external acoustic transducer can communicate with a processor to deliver sound data to a display device. It is also to be understood that the internal acoustic transducer can transmit acoustic signals, while the external acoustic transducer can receive acoustic signals. The types of acoustic transducers that can transmit acoustic signals include speakers, a piezoelectric device, etc., while the types of transducers that can receive acoustic signals include microphones, such as, but not limited to, MEMS microphones, dynamic moving-coil microphones, electret condenser microphones, ribbon microphones, magnetostrictive transducers, and piezoelectric transducers such as, by example, polyvinylidene fluoride (PVDF) microphones. A catheter guidance system and a method for accurately placing a catheter in the digestive tract or respiratory tract are also contemplated by the present invention.

The present inventors have found that the tubing assembly, catheter guidance system, and method described in more detail herein allow for the sound data captured in real-time via one or more acoustic transducers to determine if the distal end of the catheter is placed within the digestive tract (e.g., the epiglottis, esophagus, stomach, intestines, etc.) rather than placed within the respiratory system (e.g., the trachea, bronchi, lungs, etc.), where such placement could be harmful and even fatal to a patient. Further, the present inventors have found that because the acoustic transducers of the present invention can obtain measurements and communicate those measurements to processor and ultimately a display device or other communication device (e.g., a phone, pager, etc.) in real time, the placement of the catheter can be confirmed within seconds of a catheter placement procedure, which can save valuable time, resources, and cost while at the same time limit patient risk in the event of the erroneous placement of the catheter.

Specifically, the present inventors have found that capturing and monitoring sound data in real-time with an external microphone from sounds generated inside and/or with an internal microphone from sounds generated outside allows for the efficient and accurate placement of the catheter within the digestive tract at a low cost. This is facilitated by the acoustic transducers of the catheter guidance system of the present invention, as the catheter passes through the body. For instance, an external acoustic transducer placed outside the patient's body, e.g., on the throat or xyphoid process, can transmit sound data (e.g., sound waves that propagate from the external acoustic transducer that can be captured by the internal acoustic transducer located at a distal end of the catheter) as the catheter is being directed by a health care provider in to the body of a patient, where the captured sound data can then be transmitted to a display device via a processor. Alternatively, an internal acoustic transducer located at a distal end of the catheter can transmit sound data (e.g., sound waves that propagate from the internal acoustic transducer that can be captured the external acoustic transducer placed outside the patient's body, e.g., on the throat or xyphoid process) as the catheter is being directed by a health care provider in to the body of a patient, where the captured sound data can then be transmitted to a display device via a processor. In this manner, it is to be understood that the external acoustic transducer and/or the internal acoustic transducer can be bidirectional and capable of both transmitting or receiving acoustic sound data or signals. The trachea is a voluminous space filled with air. The esophagus is a collapsed muscular tube with usually little air in it. Therefore, sound waves will resonate differently when passing through each of these two structures. The health care provider can then view the captured sound data on the display device (e.g., on a spectrogram that plots the captured sound data of a graph showing frequency versus time) to determine if the catheter has been placed in the digestive tract or placed in an anatomical region of the respiratory system (e.g., the trachea, bronchi, lungs, etc.). Alternatively or additionally, a memory device that can include machine readable instructions and one or more computer programs (which, for example, may include a plurality of algorithms) can be used by the processor to process the data from the one or more acoustic transducers, where the display device can then indicate the catheter information to the health care provider in the form of a signal as to whether the catheter is placed in the digestive tract or placed within, for instance, a portion of the respiratory system. For example, a green check mark or the word "Yes" can be displayed on the screen to indicate accurate placement of the catheter within the digestive or gastrointestinal tract, while a red circle with a diagonal line through it, an "X", or the word "No" can be displayed on the screen for erroneous placement, such as placement within the respiratory system. The various features of the catheter guidance system are discussed in detail below.

Referring now to the drawings, in an embodiment illustrated in FIGS. 1-4, the catheter guidance system 2 contemplated by the present invention includes: (a) an apparatus 10 having a housing 18 which supports a controller or processor 20 and a display device 22; (b) a power cord 27 that couples the apparatus 10 to a power source 25; (c) an optional printer 28 coupled to the apparatus 10 for printing out paper having graphics which indicate catheter location information; (d) an optional non-invasive movable receiver-transmitter or transceiver 32 electronically coupled to the processor 20 by a wire, cable, signal data connection or signal carrier 63; and (e) an invasive electronic catheter unit 12 in communication with and operatively coupled to the apparatus 10 by a wire, cable, cord or electrical extension 34, which, in turn, is operatively coupled to the processor 20, where the electronic catheter unit 12 includes a tubing assembly 14 that includes a catheter 50; an acoustic transducer 46; and an optional signal generator 58 when the system 2 includes the optional non-invasive movable receiver-transmitter or transceiver 32. An external acoustic transducer 48 may additionally be included in the electronic catheter unit 12 as an attachment or alternatively separate from but in operative communication with the electronic catheter unit 12.

Figure 2:
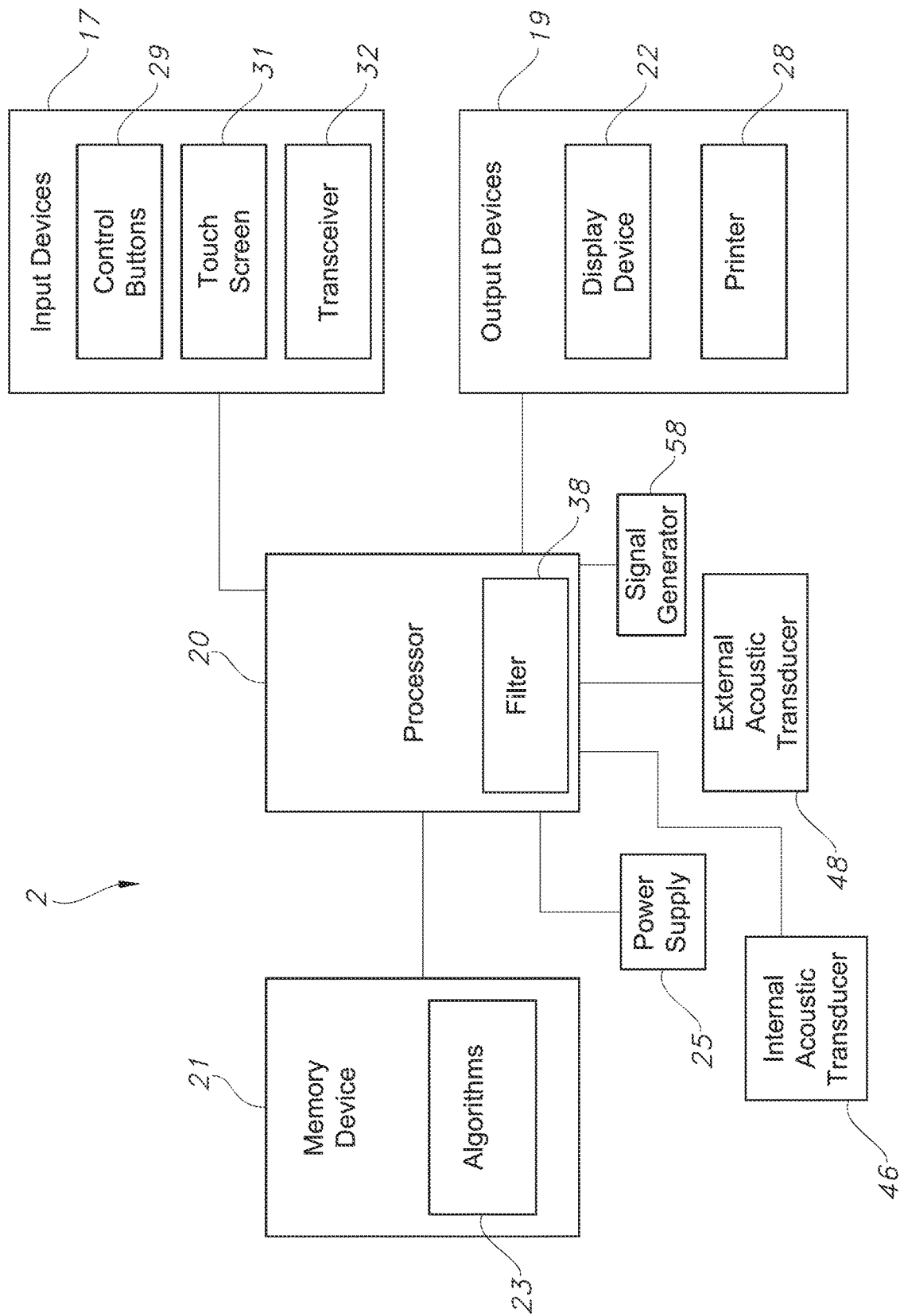
FIG. 2 is a schematic block diagram of the electronic configuration of the catheter position guidance system illustrating the processor, memory device, internal acoustic transducer, external acoustic transducer, input devices, output devices, and optional signal generating assembly according to one embodiment of the present invention.

As best illustrated in FIG. 2, the system 2, in one embodiment, includes: (a) a plurality of input devices 17 for providing input signals to the system 2 such as one or more control buttons 29, a touch screen 31, and the optional transceiver 32; (b) an acoustic transducer 46 that can continuously receive or capture sound date received from the transmitted sound waves from an external acoustic transducer 48 and/or transmit sound waves from inside or within a catheter 50 of the tubing assembly 14 in real-time; (c) an external acoustic transducer 48 that can continuously transmit and/or receive or capture sound data received from the transmitted sound waves from the acoustic transducer 46 in real-time; (d) an optional signal generator 58 which produces or generates electronic signals that are received by the transceiver 32; (e) a memory device 21 including machine readable instructions and one or more computer programs (which, for example, may include a plurality of algorithms 23) which are used by the processor 20 to instruct the external acoustic transducer 48 or the internal acoustic transducer 46 to transmit sound waves and to process the sound data captured by the other one of the acoustic transducers 46 or 48 as well as to process the signal data produced by the signal generator 58 and transmitted by the transceiver 32 if present; and (f) a plurality of output devices 19 such as the display device 22 and the printer 28 which indicate the catheter information to the health care provider, such as in the form of a graph 37 (see FIGS. 1 and 6B). The display device 22 may be any suitable display mechanism including, but not limited to, a liquid crystal display (LCD), light-emitting diode (LED) display, cathode-ray tube display (CRT) or plasma screen.

In one particular embodiment, the memory device 21 can store instructions which, when executed by the processor 20, cause the processor 20 to (i) interpret catheter 50 location and/or position information as determined and communicated by the internal acoustic transducer 46 and/or the external acoustic transducer 48 and the optional signal generating assembly 16 and the non-invasive transceiver 32, and (ii) cause the processor 20 to then instruct the system 2 to alert the health care provider either via the display device 22, auditory signals, etc. as to the accurate or inaccurate placement of the catheter 50.

Figure 3:
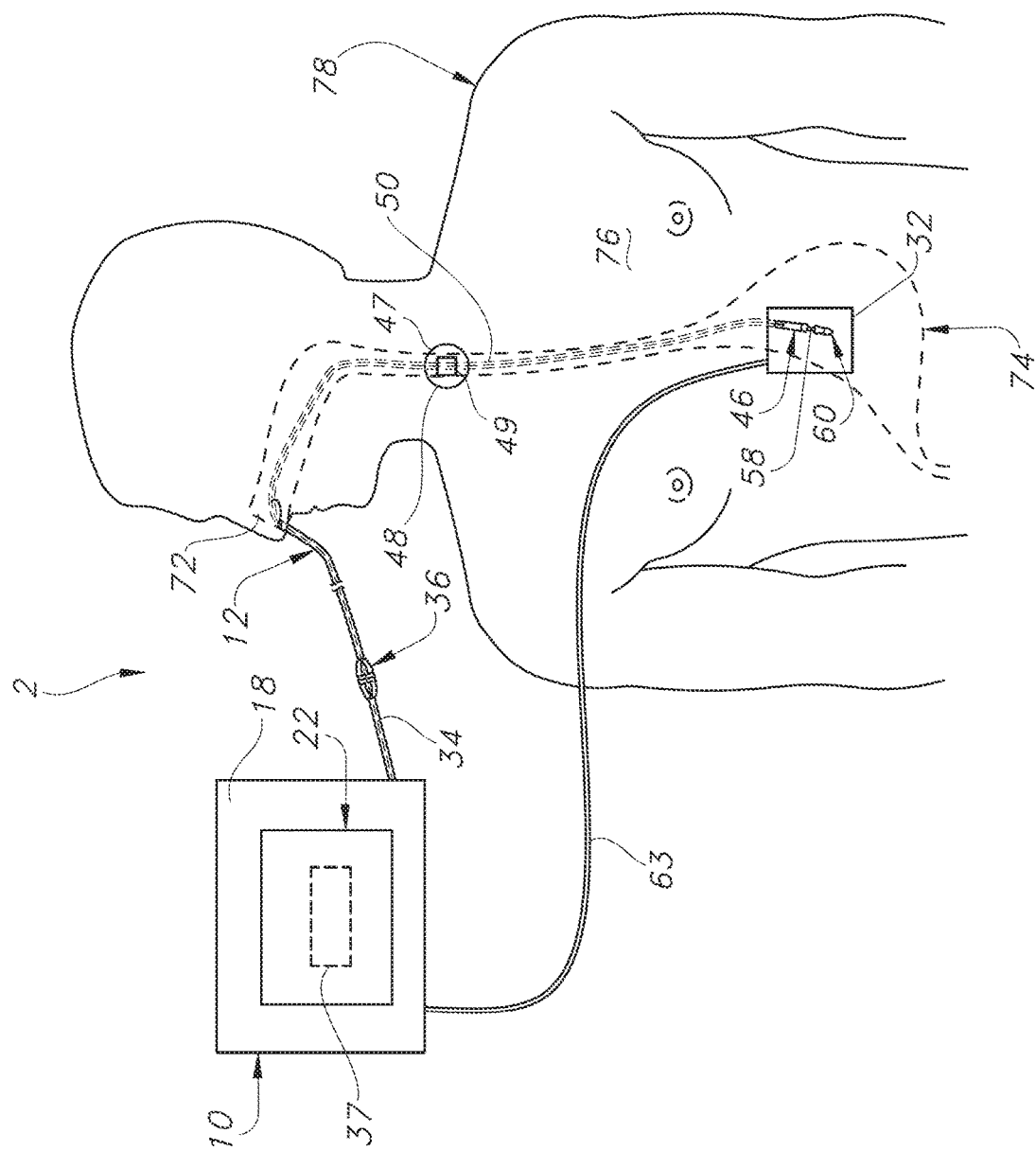
FIG. 3 is a top or plan view of the electronic catheter unit and the display device illustrating an enteral application involving a catheter inserted into a human body and indication of internal acoustic transducer and external acoustic transducer information (e.g., a graph) on the display device.

Health care providers can use the system 2 in a variety of catheter applications. In one example illustrated in FIG. 3, the system 2 is used in an enteral application. Here, a portion of the electronic catheter unit 12 is placed through an orifice 72 of the patient, such as the patient's nose or mouth. The distal end or tip 60 of the electronic catheter unit 12 can ultimately by positioned in the stomach 74. As the health care provider advances the catheter 50 of the electronic catheter unit 12 towards the patient's stomach 74, the external acoustic transducer 48 or the internal acoustic transducer 46 can continuously transmit sound waves to the opposite end of the tubing assembly, while the internal acoustic transducer 46 or the external acoustic transducer 48 can then continuously monitor for sound waves that propagate from the other one of the acoustic transducers 46 or 48 as the catheter 50 is inserted by the health care provider, whether the external acoustic transducer 48 is placed on or near the patient's body, as shown in FIGS. 1 and 3. The display device 22 and the printer 28 can indicate information related to the location of the portion of the electronic catheter unit 12 within the body 78 based on the sound data acquired by the internal acoustic transducer 46 and/or the external acoustic transducer 48, as well as information related to the shape of the pathway taken by the catheter unit 12 if the system includes the signal generator 58 and the associated non-invasive transceiver 32. It should be appreciated that the system 2 need not indicate the exact location or path of the catheter unit 12 to provide assistance to the health care provider.

Figure 4:
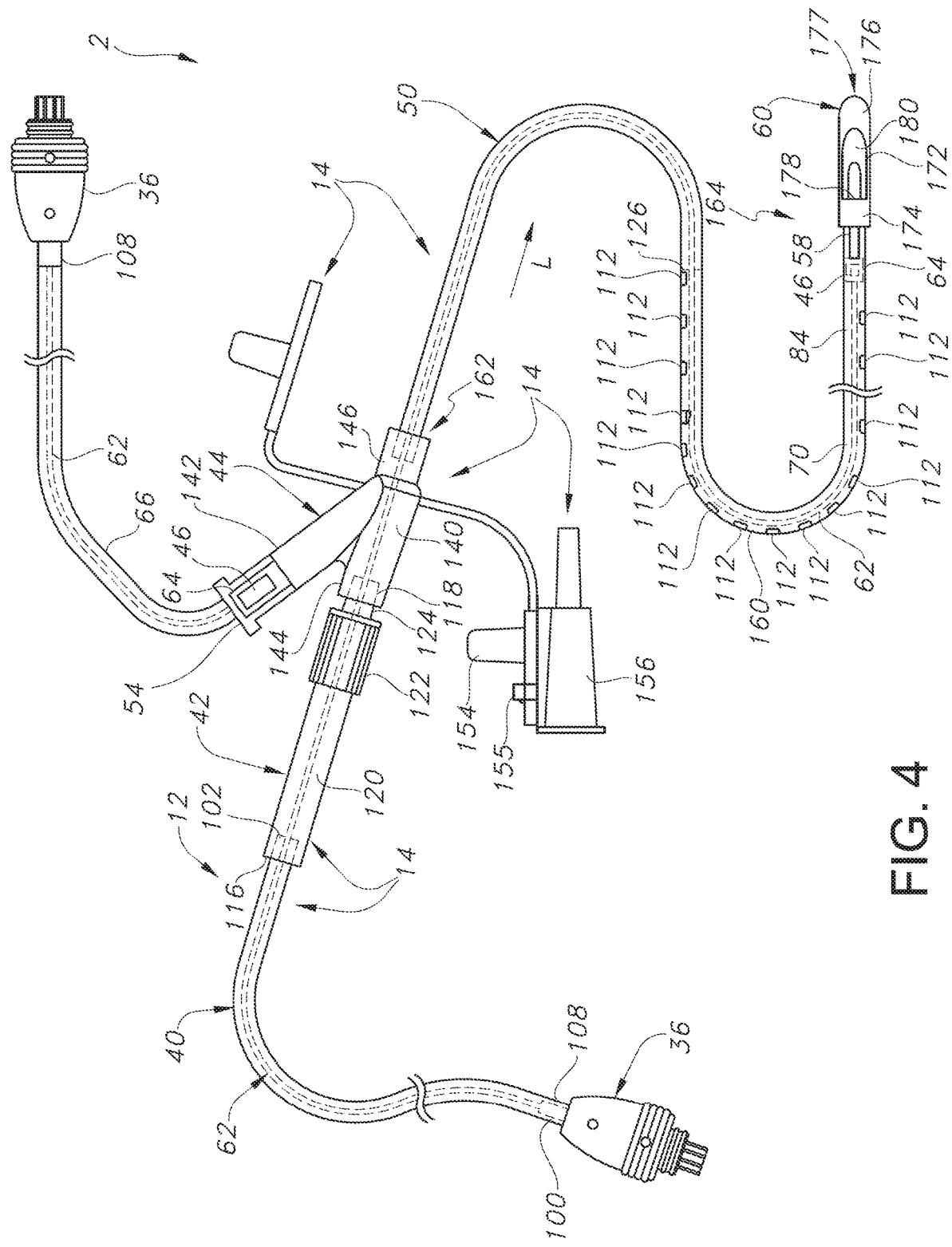
FIG. 4 is a perspective view of the electronic catheter unit illustrating the tubing assembly according to various embodiments of the present invention.

Referring to FIG. 4, in one embodiment, the electronic catheter unit 12 includes a tubing assembly 14, which includes the catheter 50 and the internal acoustic transducer 46 of the present invention, where the catheter 50 can generally extend in the longitudinal direction L. In one embodiment, the acoustic transducer 46 can be disposed within the lumen 70 of the catheter 50 at a distal end or tip 60 of the catheter 50, as shown in FIG. 4. However, it is also to be understood that the acoustic transducer 46 can be located anywhere along the length of the catheter 50, so long as the sound waves generated by the external acoustic transducer 48 can be received by the internal acoustic transducer 46 within the catheter when the external acoustic transducer 48 acts as the transmitter and the internal acoustic transducer 46 acts as the receiver of the sound waves, so long as the sound waves generated by the internal acoustic transducer 46 within the catheter 50 can be received by the external acoustic transducer 48 when the internal acoustic transducer 46 acts as the transmitter and the external acoustic transducer 48 acts as the receiver of the sound waves as the case may be, and so long as the distance from the internal acoustic transducer 46 to the distal end 60 of the catheter 50 is known.

Figure 5:
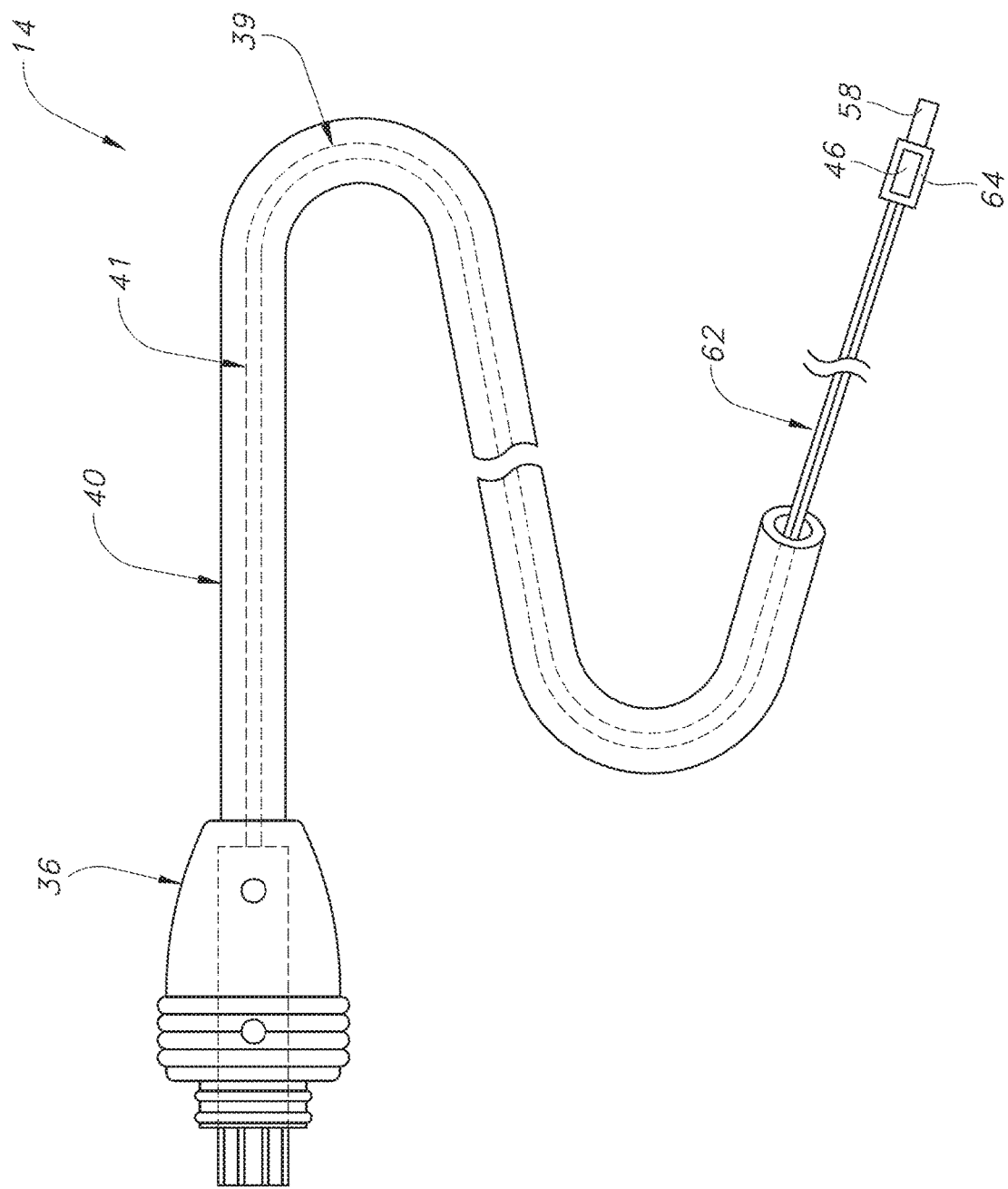
FIG. 5 is a perspective view of the internal acoustic transducer portion of the electronic catheter unit according to one embodiment of the present invention.

As best illustrated in FIGS. 4-5, in one embodiment, such as when a wired connection (e.g., a connection via a wire assembly 62 as opposed to a wireless connection, which is also contemplated by the present invention, where the internal acoustic transducer 46 includes a battery or other source of power) electrically connects the internal acoustic transducer 46 to the processor 20, the tubing assembly 14 can include (a) a tube or an electrical tubular insulator 40; (b) a mid-connector or union device 42 which receives the tubular insulator 40; (c) a multi-port connector or y-port connector 44 attachable to the union device 42; (d) a catheter 50, such as a feeding tube, connected to the y-port connector 44; and (e) a distal end or tip 60 of the catheter 50, where the internal acoustic transducer 46 can be located within the lumen 70 of the catheter 50 at the distal end or tip 60 or anywhere upstream along the length of the catheter 50.

In one embodiment, the tubular insulator 40 includes a tube having a proximal end 100 attachable to an attachment member or neck 108 of a controller coupler or electrical connector 36 and a distal end 102 receivable by the union device 42; and an internal diameter which is substantially equal to or greater than an external diameter of a wire assembly 62 described below, which can serve as the hard wired electrical connection between the acoustic transducer 46 and the processor 20, so as to slide over the wire assembly 62. In another embodiment, the tubular insulator 40 may fit relatively tightly over the wire assembly 62 so as to be secured to the wire assembly 62.

As best illustrated in FIG. 4, in one embodiment, the union device 42 includes: (a) a proximal end 116; (b) a distal end 118; (c) a position adjuster, extender or elongated neck 120 positioned between the proximal end 116 and the distal end 118; (d) a grasp or gripping member 122 positioned adjacent to the distal end 118 so as to assist users in grasping and manipulating the union device 42; and (e) an insert 124 positioned adjacent to the gripping member 122 which is received by the y-port connector 44. When assembled, the proximal end 116 of the union device 42 is coupled to the distal end 102 of the tubular insulator 40.

In one embodiment, the multi-port or y-port connector 44 includes: (a) a body 140; (b) a liquid delivery branch, medicine delivery branch or medicine branch 142 attached to the body 140 for distributing drugs, medicine or other medicinal liquids to the patient; (c) a nutrient delivery branch or feeding branch 144 attached to the body 140 and sized to receive the insert 124 of the union device 42; (d) a catheter or feeding tube connection branch 146 attached to the catheter 50; (e) a flexible or movable arm 148 attached to the body 140; and (f) a flexible or movable arm 150 attached to the body 140. In an alternative embodiment, y-port connector 44 includes additional branches for administering various nutrients or medicines to the body 78. In another alternative embodiment, the y-port connector 44 includes only a feeding branch 144 and a connection branch 146. The arm 148 has a stopper 152, and the arm 150 has a stopper 154. The stoppers 152 and 154 are sized to prevent fluid from passing through the branches 142 and 144 after such branches 142 and 144 are plugged with stoppers 152 and 154, respectively. In addition, the arm 150 includes a fastener 155 which secures a tube-size adapter 156 to the arm 150. The tube-size adapter 156 enables fluid delivery tubes (not shown) having various diameters to connect to the feeding branch 144 of the y-port connector 44.

As illustrated in FIG. 4, in one embodiment, the catheter 50 includes a feeding tube or catheter 50 with a body 160 having a proximal end 162 attached to the catheter connection branch 146 of the y-port connector 44 and a distal end 164. The proximal end 162 is insertable into the catheter connection branch 146 of the y-port connector 44 so as to bring the catheter 50 into fluid communication with the y-port connector 44.

As also shown in FIG. 4, in one embodiment, the end member, bolus or tip 60 is attached to the distal end 164 of the catheter 50. The tip 60 includes a body 172 having a collar 174 and an end member 176. The body 172 defines a passage 178 and an opening 180. The opening 180 is positioned between the collar 174 and the end member 176. A portion 177 of the end member 176 can have a rounded shape. The shape of the passage 178 and opening 180 of the tip 60 is configured to facilitate the flow of fluid from the catheter 50 into the patient's body while decreasing the likelihood that the opening 180 will become clogged.

The tubular connector 40, union device 42, y-port connector 44, catheter 50, and tip 60 can be made from any suitable polymer or plastic material including, but not limited to, polyamide, polyethylene, polypropylene, polyurethane, silicone and polyacrylonitrile.

Referring still to FIGS. 1 and 4, when the internal acoustic transducer 46 is located in the lumen 70 of the catheter 50 such as its distal end 60, the acoustic transducer 46 can be electrically connected to the processor 20 via an electrical connection in the form of a wire assembly 62 that runs through the tubular insulator 40 described above to an electrical connector or controller coupler 36, discussed in more detail below. This arrangement can also be used when the electrical connection from the acoustic transducer 46 to the processor 20 is wireless.

Turning now to the specifics of the internal acoustic transducer 46 and referring to FIGS. 1, 4, and 5, a controller coupler or an electrical connector 36 can be operatively connected to the electrical extension 34 and an elongated wire assembly 62 can be operatively coupled to the electrical connector 36 to form a wired connection between the acoustic transducer 46 and the processor 20, although it is to be understood that the electrical connection between the processor 20 and the acoustic transducer 46 can also be wireless provided that the acoustic transducer 46 has its own power source, such as a battery. Further, a wire or elongated stiffener 39 can be attached to the connector 36 and can serve as a support for the wire assembly 62 when it is inserted into the body 160 of the catheter 50 or the tubing 66. Further, the tubular insulator 40 described above can cover a portion 41 of the wire assembly 62 positioned adjacent to the connector 36 in the embodiment where the acoustic transducer 46 is positioned within the lumen 70 of the catheter 50. In any event, the electrical connector or controller coupler 36 can provide the electrical connection between the apparatus 10 and the acoustic transducer 46 when the acoustic transducer 46 is hard wired to the catheter guidance system 2 via the wire assembly 62.

Turning now to the specific configuration for the internal acoustic transducer 46, although any suitable acoustic transducer for receiving sound waves that propagate from the external acoustic transducer 48 and/or transmitting sound waves that propagate from the distal end 60 of the catheter 50 that can withstand the environmental conditions of the body can be used in the catheter guidance system 2 of the present invention, in one particular embodiment, such as when the internal acoustic transducer is receiving sound waves from the external acoustic transducer 48, the acoustic transducer 46 can be in the form of a microphone. In one particular embodiment, the microphone can be a MEMS (microelectro-mechanical system) microphone having a small footprint such that it can be placed within the lumen 70 of the catheter 50 or any other suitable location within the tubing assembly 14. Specifically, benefits of the use of a MEMS microphone include a high signal to noise (SNR) ratio, low power consumption, good sensitivity, and a small size. Further, MEMS microphones exhibit almost no change in performance after reflow soldering and have excellent temperature characteristics. In general, MEMS microphones use acoustic sensors that are fabricated on semiconductor production lines using silicon wafers and highly automated processes. Layers of different materials can be deposited on top of a silicon wafer, after which any unwanted material is then etched away, creating a moveable membrane and a fixed backplate over a cavity in the base wafer. The sensor backplate is a stiff perforated structure that allows air to move easily through it, while the membrane is a thin solid structure that flexes in response to the change in voltage or capacitance applied to the microphone. A change in the amount of capacitance between the membrane and the backplate is generated by a change in voltage applied as controlled by the processor, which is translated into movement of the membrane that generates the sound waves. For instance, the membrane may be formed from a piezoelectric material such as polyvinylidene fluoride polymer (PVDF). Meanwhile, when the internal acoustic transducer 46 is in the form of a transmitter that transmits sound waves from the distal end 60 of the catheter 50 to the external acoustic transducer 48, the internal acoustic transducer 46 can be in the form of a speaker or a piezoelectric transducer.

Turning now to the specifics of the external acoustic transducer 48, as shown in FIGS. 1 and 3, the external acoustic transducer 48 can be placed on the patient's body. For instance, the external acoustic transducer 48 can include a housing 49 and an attachment 47. The attachment 47 can be directly affixed to the subject's body 10 so that the external acoustic transducer 48 maintains a fixed reference point in relation to the patient's body. Thus, if the patient moves, the external acoustic transducer 48 moves with the patient to maintain a static frame of reference with respect to the particular patient. The attachment 47 can be positioned on a surface of the housing 49. For example, the attachment 47 can include an adhesive material that is configured to affix the housing 49 to the skin of the subject, a patch on the subject's body, or a garment worn by the subject. The adhesive material can be an adhesive substrate that can be adhesive on both sides such that it adheres to the surface of the housing 49 on one side and to a subject's body or garment on the other side. When the attachment 47 is adhesive material adhered to the surface of the housing 49, it may additionally include a peelable protective sheet covering the entire adhesive material. The peelable protective sheet can be removed prior to affixing the adhesive attachment 47 to the patient or the patient's garment. For instance, the attachment 47 can be similar to an EKG pad in which the attachment 47 includes an adhesive sheet surrounding the housing 49 such as in a donut shape. In other embodiments, the attachment 47 can include a clip, pin, magnet, hook and loop system, or any other suitable means for affixing the housing 49 of the external acoustic transducer 48 to the patient's body or garment. By using an attachment 47 on the external acoustic transducer 48 that can affix the external acoustic transducer 48 to the patient's body or garment, the frame of reference of the measurement of the sound waves either transmitted to or received from the internal acoustic transducer 46 can remain stationary with the patient's body. Alternatively, the external acoustic transducer 48 can be placed near the patient's body, such as at the patient's bedside. In some embodiments, the external acoustic transducer 48 may be incorporated into the housing 18 of the system 2.

Turning now to the specific configuration for the external acoustic transducer 48, although any suitable transducer for transmitting sound waves and/or receiving sound waves that propagate from the internal acoustic transducer 46 at the distal end 60 of the catheter 50 that can withstand the environmental conditions of the body can be used in the catheter guidance system 2 of the present invention, in one particular embodiment, such as when the external acoustic transducer is transmitting sound waves to the internal acoustic transducer 46, the external acoustic transducer 48 can be in the form of a speaker, a piezoelectric transducer, or any other suitable transmitter. In one particular embodiment, the speaker can be a MEMS speaker or any other suitable speaker that can be disposed on or near the patient's body having a small footprint such that it can be placed in a housing 49 configured to be placed on or near the patient's body. Specifically, benefits of the use of a MEMS speaker include a high signal to noise (SNR) ratio, low power consumption, good sensitivity, and a small size. Further, MEMS speakers exhibit almost no change in performance after reflow soldering and have excellent temperature characteristics. In general, MEMS speakers use acoustic sensors that are fabricated on semiconductor production lines using silicon wafers and highly automated processes. Layers of different materials can be deposited on top of a silicon wafer, after which any unwanted material is then etched away, creating a moveable membrane and a fixed backplate over a cavity in the base wafer. The sensor backplate is a stiff perforated structure that allows air to move easily through it, while the membrane is a thin solid structure that flexes in response to the change in air pressure caused by sound waves. Changes in air pressure created by sound waves cause the thin membrane to flex while the thicker backplate remains stationary as the air moves through its perforations. The movement of the membrane creates a change in the amount of capacitance between the membrane and the backplate, which is translated into an electrical signal by an application-specific integrated circuit (ASIC) located inside the MEMS speaker.

Whether a MEMS microphone, speaker, or both is used in the internal acoustic transducer 46 and/or the external acoustic transducer 58 of the present invention, the ASIC inside a MEMS device typically uses a charge pump to place a fixed charge on the microphone or speaker membrane. The ASIC then measures the voltage variations caused when the capacitance between the membrane and the fixed backplate changes due to the motion of the membrane in response to sound waves propagated from the internal acoustic transducer 46 or the external acoustic transducer 48 as the catheter 50 is inserted to the desired location in the body 78. When the MEMS device is an analog device, the device produces an output voltage that is proportional to the instantaneous air pressure level. The design of an analog MEMS device requires careful design of the PCB and cables to avoid picking up noise between the device output and the input of the integrated circuit receiving the signal, and a low noise audio analog to digital converter may be needed to convert the output of analog MEMS device into a digital format for transmission and processing via the processor 20.

Meanwhile, digital MEMS devices have digital outputs that switch between low and high logic levels. Most digital devices use pulse density modulation (PDM), which produces a highly oversampled single-bit data stream. The density of the pulses on the output of a device using pulse density modulation is proportional to the instantaneous air pressure level. Digital MEMS device outputs are relatively immune to noise, but signal integrity can still be a concern due to distortion created by parasitic capacitance, resistance, and inductance between the microphone output and the system on chip (SoC).

Thus, whether the internal acoustic transducer 46 and/or the external acoustic transducer 48 is in the form of an analog or digital MEMS speaker or microphone, the sound data or signals transmitted from or received by the internal acoustic transducer 46 and/or the external acoustic transducer 48 to the processor 20 may first pass through a filter assembly 38 to remove unwanted noise from the captured sound data and amplify the frequencies of interest before being processed and presented to the display device 22 via the processor 20 and its associated algorithms 23 stored in the memory device 21, although when the internal acoustic transducer 46 and/or the external acoustic transducer 48 is a digital sensor, a filter 38 may not be needed and the sound data or signals can be transmitted directly to the processor 20. The filter 38 can be in the form of a hardware filter, a software filter, or a combination thereof. Further, the filter 38 can include a combination of a low pass filter and a high pass filter. When the internal acoustic transducer 46 and/or the external acoustic transducer 48 is an analog sensor, the filter 38 can include a hardware low pass filter and a hardware high pass filter. In addition, once the sound data or signals are filtered, an analog to digital converter can convert the sound data or signals to digital format, where the signal can then be sent to the processor 20 for further analysis. Meanwhile, when the internal acoustic transducer 46 and/or the external acoustic transducer 48 is a digital sensor, the filter 38 can be a digital software filter that can be implemented to remove both low frequency and high frequency bands. Regardless of the specific type of filter 38 utilized, the filter 38 can be used to optimize the quality of the sound data or signals captured by the receiving transducer of either the internal acoustic transducer 46 or the external acoustic transducer 48 in order to accurately determine if a catheter is placed within a digestive tract of a patient or in a respiratory tract of the patient.

In one aspect of the invention, the system 2 is able to accurately identify the placement of a catheter based on signals or sound data, such as attenuation of sound signals and/or detection of resonance frequencies, associated with the anatomy of the catheter location. For instance, the transducer functioning as the transmitter (e.g., the internal acoustic transducer 46 or the external acoustic transducer 48 as the case may be) may transmit sound waves that include a sweep of frequencies. The sweep of frequencies can be in a range from about 20 hertz to about 500 kilohertz, representing wavelengths on the order of 17 m-680 um in air, respectively; and on the order of 77 m-3 mm in water (approximating body fluid), respectively. Therefore by comparing the low frequency sounds with longer wavelengths (that significantly exceed the radial dimensions of the trachea (diameter around 2 cm) and esophageal tubes (diameter collapsed usually) and therefore will not resonate to any significant degree, in a transverse dimension as set up in the preferred embodiment described) to the higher frequency sounds with shorter wavelengths (that are of similar radial dimensions as the trachea and esophageal tubes and therefore will resonate more readily in the open trachea but less-so in the collapsed esophagus, in a transverse dimension as set up in the preferred embodiment described), the location of the internal transducer in the esophagus vs. the trachea can be distinguished. Further, the transducer functioning as the receiver (e.g., the internal acoustic transducer 46 or the external acoustic transducer 48 as the case may be) may be used to detect distinct resonance frequencies from the esophagus compared to the trachea from the sweep of frequencies delivered by the transducer functioning as the transmitter. In an alternate embodiment, if the transducers are arranged longitudinally instead, such that one is inside at the tip of the catheter and the other is outside near the mouth, then wavelengths that will resonate in proportion to the longitudinal dimensions of the trachea would be more appropriate. In such a case, the resonance frequency of the trachea typically ranges from about 275 hertz to about 350 hertz, such as from about 300 hertz to about 325 hertz (where 300 Hz has a wavelength of approximately 1.1 m at 340 m/s in air). Furthermore, by measuring and then comparing the ratio of amplitudes of the low-frequency sounds that do not resonate versus the amplitudes of the high-frequency sounds which do resonate, relative signatures for esophageal versus tracheal placement can be determined, allowing one to standardize the technique irrespective of the absolute sound volume required for detection. For example, in a large obese male patient versus a small neonate, the absolute amplitude required will be different, while the ratio of high frequency to low frequency outputs detected can provide a signature specific to that location (along the esophagus or trachea), rather than relying on the absolute amplitudes detected which can be confounded by patient size, body habitus, etc. Additionally or alternatively, the internal acoustic transducer 46 or the external acoustic transducer 48 may detect different signature of frequencies based on placement in the esophagus compared to the trachea. For instance, the internal acoustic transducer 46 or the external acoustic transducer 48 may detect a sound signature indicative of sounds of breathing associated with inspiration and expiration when the catheter is positioned in the trachea. The internal acoustic transducer 46 or the external acoustic transducer 48 may also deliver repeated sound patterns at a particular frequency or range of frequencies. The sound patterns delivered by the acoustic transducer that is functioning as the transmitter (e.g., either the internal acoustic transducer 46 or the external acoustic transducer 48) may be detected by the other of the acoustic transducers that is functioning as the receiver (e.g., either the internal acoustic transducer 46 or the external acoustic transducer 48) by summing the sound signals together, temporally matching the frequency patterns, and detecting the particular frequencies to determine a match with the delivered pattern. Regardless of the means of delivering and/or detecting the sound signals, the system 2 may include one or more high pass and/or low pass filters to filter out noise above or below the delivered frequencies.

For instance, when the one of the acoustic transducers 46 or 48 is required to identify sound data associated with inspiration and expiration, the frequency ranges of the breathing sounds associated with inspiration and expiration typically range from about 100 Hertz to about 2,000 Hertz. However, a majority of the power associated with inspiration and expiration breathing sounds falls within the range of about 100 Hertz to about 600 Hertz. On the other hand, sounds associated with the heart and muscle are typically less than about 100 Hertz. Thus, in order to accurately identify inspiration and expiration breathing sounds, filtering out frequencies less than about 100 Hertz, which would filter out those sounds associated with heart and muscle, can enable a more accurate determination of whether or not the tubing assembly of the present invention is being inserted into the respiratory tract or airway. Thus, the low pass filter used in the filter arrangement of the present invention can have a cutoff of about 100 Hertz. On the other hand, the high pass filter used in the filter arrangement of the present invention can have a cutoff of about 1800 Hertz, although it is to be understood that the low frequency and high frequency cutoffs can be adjusted as needed to optimize performance of the catheter guidance system 2 of the present invention. For instance, in some embodiments, the filter 38 can allow sound data or signals associated with frequencies ranging from about 100 Hertz to about 1800 Hertz, such as from about 125 Hertz to about 1400 Hertz, such as from about 150 Hertz to about 1000 Hertz to pass through to the processor 20 for further analysis. However, the filter 38 can be configured to allow sound data or signals associated with any frequency range suitable for the sound signals, e.g., frequency sweep or pattern, delivered by the acoustic transducer 46 or 48 that is functioning as the transmitter.

Further, in one embodiment and referring to FIG. 4, the catheter body 160 can have a plurality of markings 112 uniformly spaced along its external surface that can be used in conjunction with the internal acoustic transducer 46 and the external acoustic transducer 48 to determine accurate placement of the catheter 50. These markings 112 can function as placement markers which assist the user in assessing the depth that the catheter 50 is placed within the body 78. For instance, when the internal acoustic transducer 46 is located at the distal end 60 of the catheter 50, the markings 112 can be present from the distal end 60 of the catheter 50 to a point 126 on the catheter 50 that spans a distance that can correspond with the average distance between the trachea 92 and nostril 87 in a typical patient. As the catheter 50 is being inserted into the body 78 via the nostril 87, once the markings 112 are no longer visible outside the body 78, the user can instruct the system 2 to initiate the receiving and transmitting functions of the internal acoustic transducer 46 and the external acoustic transducer 48 and start monitoring the graphs 37 on the display device 22 to observe the sound signals plotted from sound data transmitted, received, and communicated by the acoustic transducers 46 and 48 or to start monitoring for a visual indication, auditory indication, or both that the catheter 50 has be inserted into the correct (e.g., digestive tract) or incorrect location (e.g., respiratory tract). In an alternative embodiment, these markings 112 can assist the user in measuring the flow or distribution of liquid to or from the patient.

Now that the specific components of the catheter guidance system 2 have been discussed in detail, a method of using the catheter guidance system 2 of the present invention in order to verify the accurate placement of a catheter 50 used for enteral feeding in the digestive tract is discussed in more detail below with reference to FIGS. 6A-7B.

Generally, the method for determining if the catheter 50 is accurately placed within a digestive tract of a body 78 of a patient includes inserting a distal end of the tubing assembly 14 (e.g., the distal end or tip 60 of the catheter 50) into an orifice 72 of the body 78, such as a nostril 87 of the patient's nose. As described above, the tubing assembly 14 can include the catheter 50 and the internal acoustic transducer 46. Once the tubing assembly 14 is inserted into the orifice 72 of the body 78, the internal acoustic transducer 46 can be electrically connected to a processor 20 via a wired connection, such as the wire assembly 62, although a wireless connection is also contemplated by the present invention such that no wire assembly 62 or controller coupler 36 is required).

Next, the internal acoustic transducer 46 can be activated, such as by providing power to the internal acoustic transducer 46, and the internal acoustic transducer 46 can then begin to deliver a sweep of frequencies if it is functioning as a transmitter or can begin to receive sound waves it is functioning as a receiver. At or around the same time, the external acoustic transducer 48 can be activated, such as by providing power to the external acoustic transducer 48 and connecting the external acoustic transducer 48 to the processor 20. The external acoustic transducer 48 can then begin to measure the acoustic signals received from the internal acoustic transducer 46 if it is functioning as a receiver or can begin to deliver a sweep of frequencies if it is functioning as a transmitter. Further, one or both of the internal acoustic transducer 46 and the external acoustic transducer 48 can communicates with the processor 20 via a wired connection or the wireless connection to deliver the acquired sound data to the processor 20 in real-time.

In addition, a display device 22 is coupled to the processor 20 and displays the sound data communicated to the processor 20 by the internal acoustic transducer 46, the external acoustic transducer 48, or both for a health care provider to use during the catheter insertion procedure, where the sound data may first pass through a filter 38 to remove unwanted noise and amplify the frequencies of interest. The filtered data can then be presented as a graph 37 on the display device 22, where differences in the frequency response can be easily identified by the health care provider via the graphs 37 on the display device 22. Alternatively or additionally, the memory device 21 can store instructions which, when executed by the processor 20, cause the processor 20 to interpret catheter 50 location and/or position information as determined and communicated by the internal acoustic transducer 46, the external acoustic transducer 48, or both, and the optional signal generating assembly 16 and the non-invasive transceiver 32 and cause the processor 20 to then instruct the system 2 to alert the health care provider either via the display device 22, auditory signals, etc. as to the accurate or inaccurate placement of the catheter 50

Specifically, the graphs 37 can plot the frequency response of the sound waves as they are transmitted by the external acoustic transducer 48 and received by the internal acoustic transducer 46 and vice versa in order to determine if the catheter 50 is placed in the esophagus/digestive tract or trachea/lungs/respiratory tract. Further, in order for such information to be displayed or otherwise communicated by the display device 22, a memory device 21 stores instructions which, when executed by the processor 20, cause the processor 20 to (i) interpret the sound data communicated by internal acoustic transducer 46 and the external acoustic transducer 48 and (ii) cause the display device 22 to communicate whether or not the catheter 50 is accurately placed, e.g., within the digestive tract of the patient, based on the interpretation of the sound data.

The present inventors have found that the distinctions between the frequency response based on the anatomical location of the catheter 50, as identified by the internal acoustic transducer 46 and/or the external acoustic transducer 48, when the distal end or tip 60 of the enteral catheter 50 is placed within the digestive tract or respiratory system are allow for an efficient and possibly life-saving determination of accurate enteral feeding catheter 50 placement in the digestive tract, where erroneously placing the catheter in the respiratory system would deliver fluid into the lungs, which can have fatal consequences.

Figure 6A:
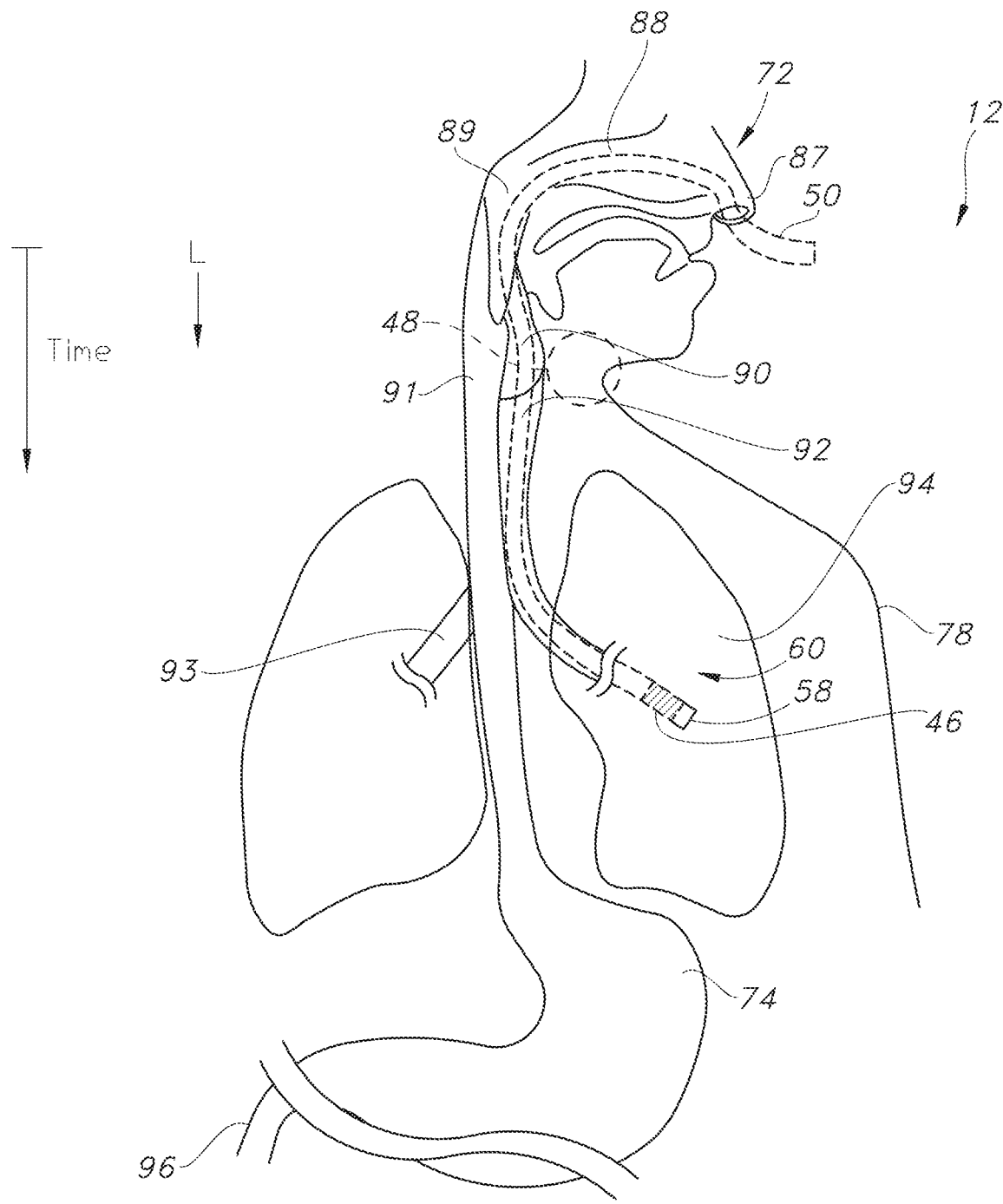
FIG. 6A is a top or plan view of a portion of the electronic catheter unit illustrating an enteral application involving the mistaken insertion of a catheter into the trachea and/or other anatomical regions of the respiratory tract (e.g., the lung) of a patient, where the anatomical location of the catheter within the body can be monitored via sound data generated and captured or received by either the first acoustic transducer and/or the second acoustic transducer, respectively, of the present invention.
Figure 6B:
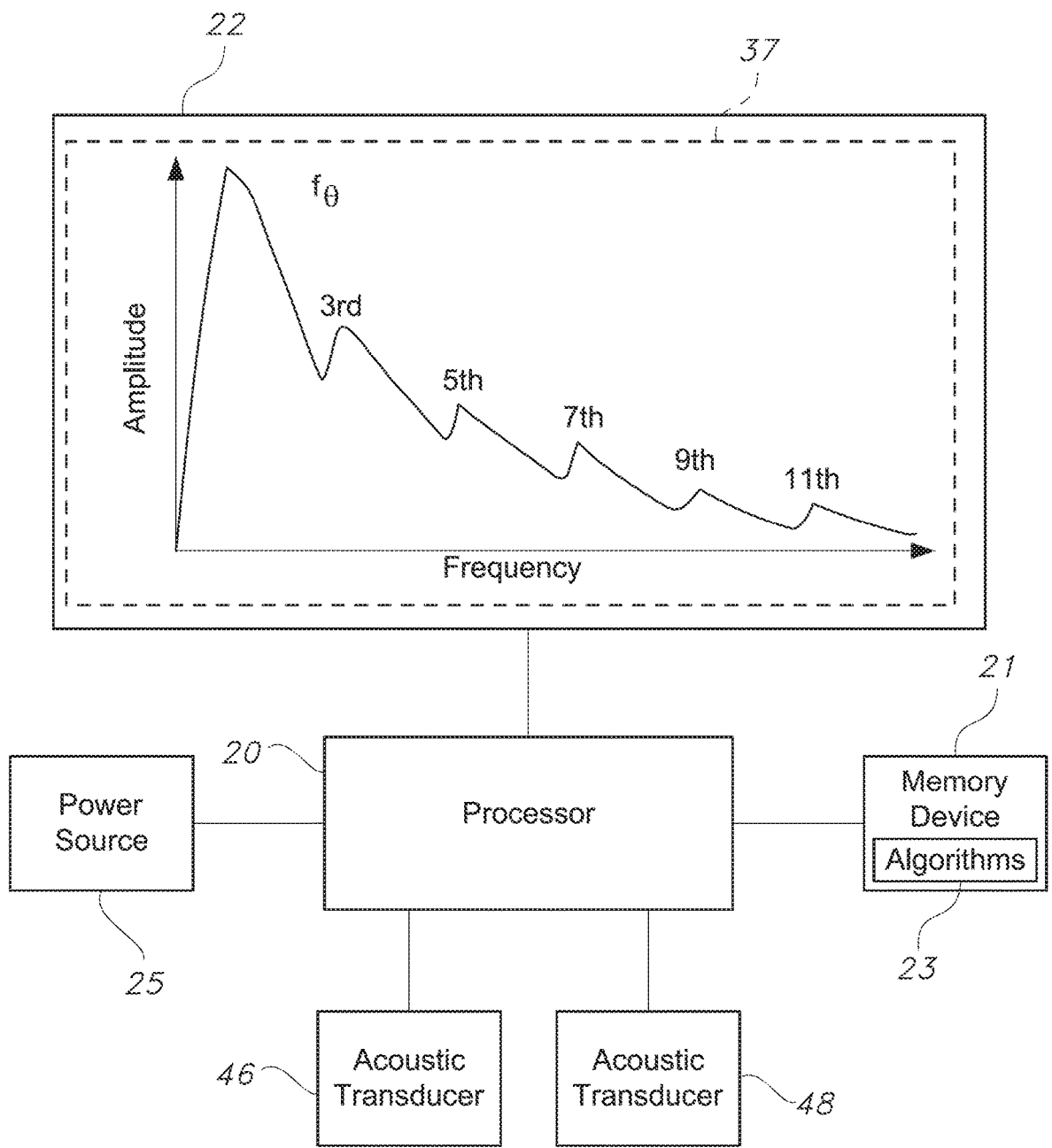
FIG. 6B is a schematic view of the catheter guidance system of the present invention as the system captures resonance frequency data associated with placement of the catheter in the respiratory tract as shown in FIG. 6A in real-time via the acoustic transducers of the present invention.

For instance, as shown in FIGS. 6A and 6B, when the distal end or tip 60 of the catheter 50 is inserted into the nostril 87 of the patient and is advanced through the nasal cavity 88, past the nasopharynx 89, and into the trachea 92 just past the epiglottis 90, and then into the bronchi 93 or lungs 94, as the external acoustic transducer 48 or the internal acoustic transducer 46 transmits a frequency sweep and the internal acoustic transducer 46 or the external acoustic transducer 48 is continuously receiving, recording, and/or processing sound waves propagating from the other of the transducers, the frequency response graph 37 (FIG. 6B) displayed or otherwise communicated by the processor 20, such as via the display device 22, may show a distinct frequency response of the trachea 92 when the distal end or tip 60 of the catheter 50 travels into the respiratory system. Specifically, the processor 20, memory device 21, and algorithms 23 can be used to analyze the data received from one or both of the acoustic transducers 46 and 48 to cause a graph 37 to be shown on the display device 22, where the frequency and amplitude response are indicative of placement of the catheter 50 in the trachea 92. Specifically, the frequency vs. amplitude graph 37 shows attenuation in amplitude from the harmonic frequency $f_\theta$ to the $3^{rd}$, $5^{th}$, $7^{th}$, $9^{th}$, and $11^{th}$ harmonic frequencies. This type of frequency response with a trend of a decreasing amplitude but with sharp spikes of increased frequencies at the harmonic frequencies is indicative of the behavior of the ultrasound waves as the waves travel through air between rings of the cartilaginous tissue of the trachea 92. With insertion of the enteral catheter 50 inaccurately into the respiratory system, the inaccurate placement will quickly become apparent to the health care provider within a matter of seconds of the insertion procedure (e.g., once the distal end or tip 60 reaches the trachea 92, the bronchi 93, or the lungs 94) as the distal end or tip 60 of the catheter 50. At this point, the health care provider can be alerted to remove the tubing assembly 14 from the respiratory system and start a new procedure to accurately place the distal end or tip 60 of the catheter 50 into the digestive tract for enteral feeding.

Figure 7A:
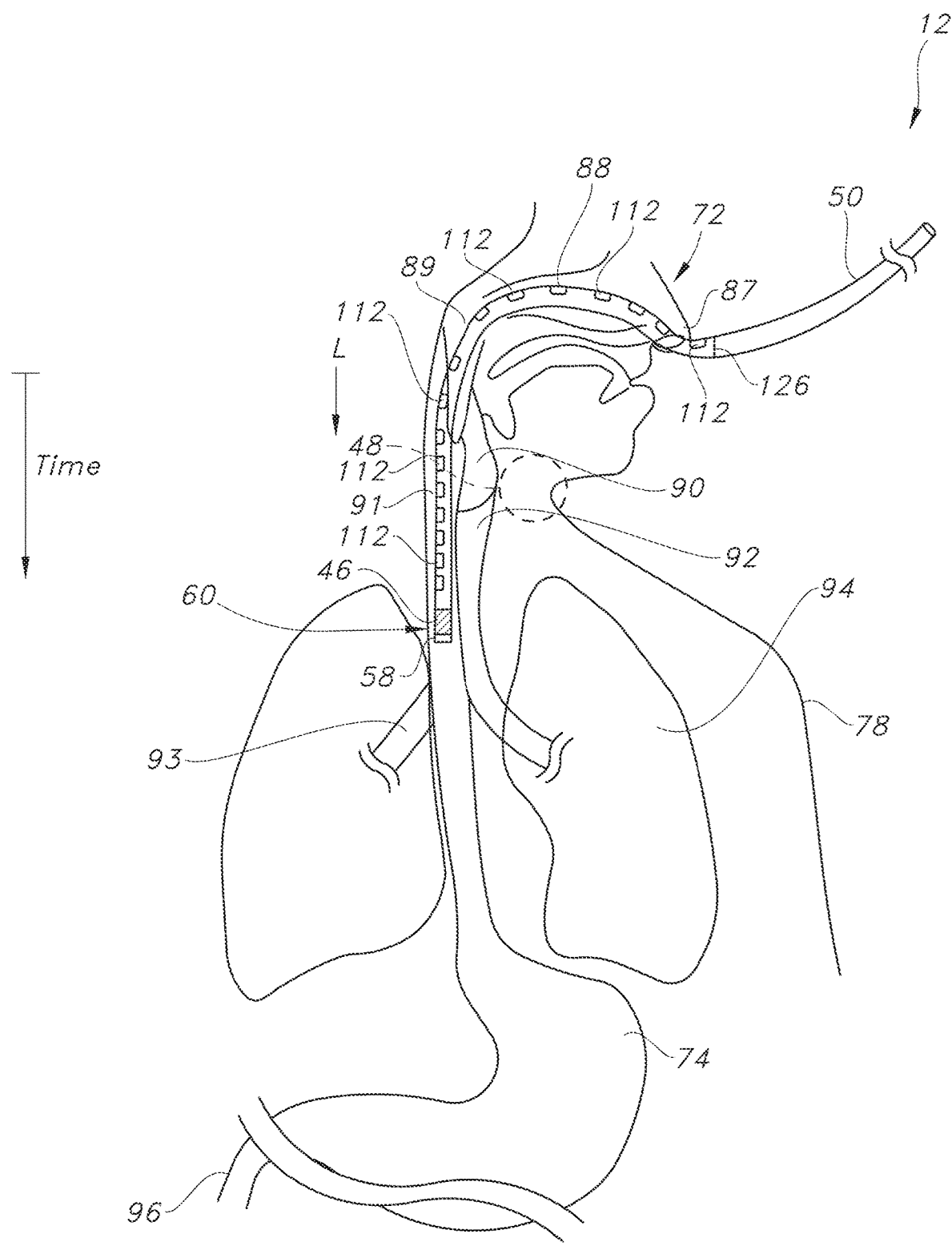
FIG. 7A is a top or plan view of a portion of the electronic catheter unit illustrating an enteral application involving the correct insertion of a catheter into the esophagus of a patient, where the anatomical location of the catheter within the body can be monitored via sound data generated and captured or received by the first acoustic transducer and/or the second acoustic transducer, respectively, of the present invention.
Figure 7B:
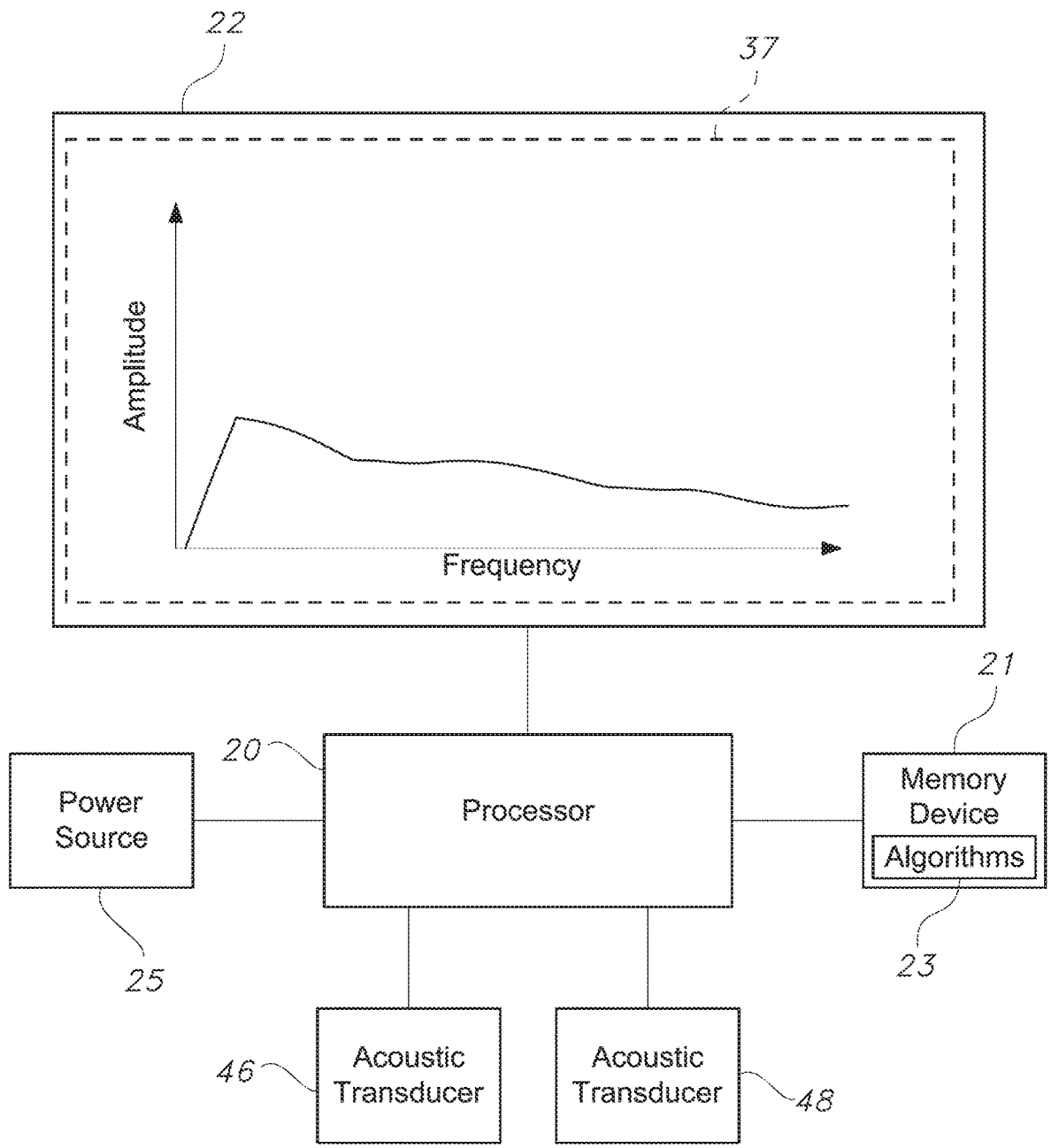
FIG. 7B is a schematic view of the catheter guidance system of the present invention as the system captures resonance frequency data associated with placement of the catheter in the digestive tract as shown in FIG. 7A in real-time via the acoustic transducers of the present invention.

In contrast, as shown in FIGS. 7A and 7B, when the distal end or tip 60 of the catheter 50 is inserted into the nostril 87 of the patient and is advanced through the nasal cavity 88, past the nasopharynx 89, and into the esophagus 91, as the external acoustic transducer 48 or the internal acoustic transducer 46 transmits a frequency sweep and the internal acoustic transducer 46 or the external acoustic transducer 48 is continuously receiving, recording, and/or processing sound waves propagating from the other of the transducers, the frequency response graph 37 (FIG. 6B) displayed or otherwise communicated by the processor 20, such as via the display device 22, may show a distinct frequency response of the esophagus 91 when the distal end or tip 60 of the catheter 50 travels into the digestive system. Specifically, the processor 20, memory device 21, and algorithms 23 can be used to analyze the data received from one or both of the acoustic transducers 46 and 48 to cause a graph 37 to be shown on the display device 22, where the frequency and amplitude response are indicative of placement of the catheter 50 in the esophagus 91. Specifically, the frequency vs. amplitude graph 37 shows a sharp increase in amplitude then a gradual attenuation in amplitude as the frequency increases. This type of frequency response with a trend of a gradually decreasing amplitude is indicative of the behavior of the ultrasound waves as the waves travel through muscle and tissue in the esophagus 91. This can confirm to a provider that the catheter 50 has been placed properly.

Additionally or alternatively, the external acoustic transducer 48 or the internal acoustic transducer 46 can transmit acoustic signals at a particular frequency and amplitude, and the other of the acoustic transducers 46 or 48 can be configured to receive the acoustic signals and send sound data to the processor 20 in order to determine how much the transmitted acoustic signals are attenuated. The amount of attenuation of the acoustic signals can indicate whether the catheter 50 is located in the digestive tract, e.g., esophagus 91, or in the respiratory tract, e.g., trachea 92. As shown in FIGS. 6A and 7A, the respiratory tract, e.g., trachea 92, is nearer to the surface of the chest of the patient where the external acoustic transducer 48 may be positioned than the digestive tract, e.g., esophagus 91. As a result, when the internal acoustic transducer 46 of the catheter 50 is located in the digestive tract, as shown in FIG. 7A, the acoustic signals may be attenuated more than if the internal acoustic transducer 46 of the catheter 50 is disposed in the respiratory tract, as the acoustic signals must travel further from the digestive tract to reach the external acoustic transducer 48 if the internal acoustic transducer 46 is the transmitter and vice versa if the external acoustic transducer 48 is the transmitter. Similarly, a time-of-flight calculation may be determined by comparing the time at which the external acoustic transducer 48 or the internal acoustic transducer 46 transmits an acoustic signal and the time after which the other of the acoustic transducers 46 or 48 receives that acoustic signal.

Further, as an alternative or in addition to generating acoustic signals via the external acoustic transducer 48 or the internal acoustic transducer 46 and recording sound data received via the other of the acoustic transducers 46 or 48 over time and observing the sound data on a graph 37 or other type of plot, the health care provider can also verify accurate placement of the catheter 50 in the esophagus 91 rather than the trachea 92 by observing for the presence or absence of a plurality of markings 112 uniformly spaced along the external surface of the catheter 50. As described above, such markings 112 can be used in conjunction with the internal acoustic transducer 46 and the external acoustic transducer 48 to determine accurate placement of the catheter 50. These markings 112 can function as placement markers which assist the user in assessing the depth that the catheter 50 is placed within the body 78. For instance, when the internal acoustic transducer 46 is located at the distal end 60 of the catheter 50, the markings 112 can be present from the distal end 60 of the catheter 50 to a point 126 on the catheter 50 that spans a distance that can correspond with the average distance between the trachea 92 and nostril 87 in a typical patient. As the catheter 50 is being inserted into the body 78 via the nostril 87, once the markings 112 are no longer visible outside the body 78, the health care provider can be alerted to start monitoring the graphs 37 on the display device 22 to observe the spectrograms plotted from sound data measured by the internal acoustic transducer 46 or the external acoustic transducer 48 or to start monitoring for a visual indication, auditory indication, or both that the catheter 50 has be inserted into the correct (e.g., digestive tract) or incorrect location (e.g., respiratory tract).

Regardless of the particular method by which proper placement of the catheter 50 is determined, once the distal end or tip 60 of the catheter 50 has been accurately placed within the desired location in the digestive tract, the health care provider can then optionally remove the internal acoustic transducer 46 and the external acoustic transducer 48, particularly when the internal acoustic transducer 46 is located within the lumen 70 of the catheter and includes a wired connection, where the wire assembly 62 electrically connects the internal acoustic transducer 46 to the processor 20 via the electrical connector or controller coupler 36, while the position of the catheter 50 is maintained. The health care provider can then attach medicine and nutritional delivery tubes to the y-port connector 44 for introducing fluids into the body (e.g., digestive tract) for medical treatment. On the other hand, if the internal acoustic transducer 46 is wireless, the internal acoustic transducer 46 and the external acoustic transducer 48 can optionally be left in place, and the health care provider can then attach medicine and nutritional delivery tubes to the y-port connector 44 for introducing fluids into the body (e.g., digestive tract) for medical treatment.

Moreover, in conjunction with the internal acoustic transducer 46 and external acoustic transducer 48 described herein, the system 2 also contemplates the use of an optional signal generator 58 and associated transceiver 32 that can be used to track the position of the distal end 60 of the catheter 50 as it is being inserted into the patient's body 78. In one embodiment, the signal generator 58, which is located at the distal end 60 of the catheter and can be connected to the apparatus 10 via the controller coupler/electrical connected 36 and the wire assembly 62 (see FIGS. 1, 3, and 4), can be formed through one or a plurality of spirals or coils of wires. Further, the apparatus 10 can be configured to transmit electrical current through the wires such that the current travels in a circular path defined by the coils. This circular motion of current produces an electromagnetic field. In operation, when the apparatus 10 sends electrical current to the coils of the signal generator 58, the coils then transmit a signal or electromagnetic field capable of being detected by the non-invasive transceiver 32. The transceiver 32 then detects the electromagnetic field or signal generated by the signal generator 58 inside the patient's body 78 and the system 2 analyzes the resulting information to cause the display device 22 and the printer 28 to produce additional graphics 37 which can assist the health care provider in a catheter placement procedure in conjunction with sound data acquired by the internal acoustic transducer 46 and/or the external acoustic transducer 48. For instance, the system 2 can include a memory device 21 including machine readable instructions and one or more computer programs (which, for example, may include a plurality of algorithms 23) which are used by the processor 20 to process the signal data produced by the signal generator and transmitted by the transceiver 32, after which the processed data is displayed in graphical format on the display device 22 corresponding to the location of the distal end 60 of the catheter 50 within the patient's body 78. In one particular embodiment, the transceiver 32 can be used to determine the distance the signal generator 58 is from the transceiver 32 and its dept in the patient's body 78 can communicate with the display device 22 via the processor 20 to show a reference image of a non-subject body and an image of the signal generator 58 located on the display device 22 with the reference image.

It should also be appreciated that the tubing assembly, electronic catheter unit and catheter position guidance system of the present invention can be used in a variety of catheter procedures and applications. These procedures may involve the treatment of the digestive or gastrointestinal tract or other portions of the human body. These procedures may involve treatment of humans by physicians, physician assistants, nurses or other health care providers. In addition, these procedures may involve treatment of other mammals and animals by veterinarians, researchers and others.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A catheter guidance system comprising:
    (a) a processor;
    (b) a power source;
    (c) a display device;
    (d) an external acoustic transducer; and
    (e) a tubing assembly comprising:
    a catheter having a proximal end and a distal end and extending in a longitudinal direction, wherein the proximal end and the distal end define a lumen therebetween; and
    an internal acoustic transducer;
    wherein the internal acoustic transducer receives sound waves as controlled by the processor in real-time via an electrical connection;
    wherein the external acoustic transducer transmits the sound waves, wherein the internal acoustic transducer communicates acquired sound data to the processor in real-time via an electrical connection, and further wherein the external acoustic transducer is contained within a speaker and is configured for stationary placement on a body of a patient;
    wherein the display device is coupled to the processor and displays a graph of the sound data communicated by the internal acoustic transducer or the external acoustic transducer; and
    wherein the catheter guidance system is configured to alert a user as to placement of the catheter in a digestive tract of the patient or alert the user as to placement of the catheter in a respiratory tract of the patient by distinguishing between a frequency response associated with the placement of the catheter in the digestive tract of the patient or the placement of the catheter in the respiratory tract of the patient, wherein the frequency response associated with the placement of the catheter in the digestive tract exhibits an initial peak in amplitude followed by a gradual decrease in amplitude as frequency is increased, and wherein the frequency response associated with the placement of the catheter in the respiratory tract of the patient exhibits an initial peak in amplitude followed by an overall decrease in amplitude with spikes of increased amplitude at one or more harmonic frequencies as frequency is increased.

2. The catheter guidance system of claim 1, further comprising a memory device storing instructions which, when executed by the processor, cause the processor to (i) interpret the sound data communicated by the internal acoustic transducer or the external acoustic transducer and (ii) cause the catheter guidance system to alert the user as to placement of the catheter in the digestive tract of the patient or alert the user as to placement of the catheter in the respiratory tract of the patient based on the interpretation of the sound data.

3. The catheter guidance system of claim 1, wherein the internal acoustic transducer is located within the lumen of the catheter at the distal end of the catheter.

4. The catheter guidance system of claim 1, wherein the internal acoustic transducer is protected from fluid ingress by a flexible coating.

5. The catheter guidance system of claim 1, wherein the internal acoustic transducer is contained within a microphone.

6. The catheter guidance system of claim 1, wherein the external acoustic transducer is configured to be placed on or adjacent to the throat of the patient or the chest of the patient.

7. A method for determining if a catheter is placed within a digestive tract of a body of a patient via a catheter guidance system comprising a processor, a power source, a display device, an external acoustic transducer, and a tubing assembly, the method comprising:
 (a) inserting a distal end of the tubing assembly into an orifice of the body of the patient, wherein the tubing assembly comprises:
  the catheter, wherein the catheter has a proximal end and a distal end and extends in a longitudinal direction, wherein the proximal end and the distal end define a lumen therebetween; and
  an internal acoustic transducer;
 (b) electrically connecting the internal acoustic transducer to the processor via a wired connection or a wireless connection;
 (c) placing the external acoustic transducer on or adjacent to the patient's throat or chest, wherein the external acoustic transducer is electrically connected to the processor via a wired connection or a wireless connection;
 (d) activating the internal acoustic transducer, wherein the internal acoustic transducer receives sound waves as controlled by the processor in real-time via an electrical connection;
 (e) advancing the distal end of the catheter inside the body of the patient in a direction away from the orifice while the external acoustic transducer is activated;
 (f) activating the external acoustic transducer to transmit the sound waves, wherein the internal acoustic transducer acquires sound data from the sound waves and communicates the sound data to the processor in real-time, wherein the external acoustic transducer is contained within a speaker and is configured for stationary placement on the body of the patient; and
 (g) observing a graph of the sound data on the display device coupled to the processor, wherein the catheter guidance system is configured to alert a user as to placement of the catheter in the digestive tract of the patient or alert the user as to placement of the catheter in a respiratory tract of the patient by distinguishing between a frequency response associated with the placement of the catheter in the digestive tract of the patient or the placement of the catheter in the respiratory tract of the patient, wherein the frequency response associated with the placement of the catheter in the digestive tract exhibits an initial peak in amplitude followed by a gradual decrease in amplitude as frequency is increased, and wherein the frequency response associated with the placement of the catheter in the respiratory tract of the patient exhibits an initial peak in amplitude followed by an overall decrease in amplitude with spikes of increased amplitude at one or more harmonic frequencies as frequency is increased.

8. The method of claim 7, wherein a memory device stores instructions which, when executed by the processor, cause the processor to (i) interpret the sound data communicated by the internal acoustic transducer or the external acoustic transducer and (ii) cause the display device to communicate whether or not the catheter is placed within the digestive tract of the patient based on the interpretation of the sound data.

9. The method of claim 7, wherein the orifice of the body of the patient is a nose or a mouth.

10. The method of claim 7, wherein the internal acoustic transducer is located within the lumen of the catheter or within a sampling chamber.

11. The method of claim 7, wherein the internal acoustic transducer is contained within a microphone, and wherein the internal acoustic transducer is protected from fluid ingress by a flexible coating.

* * * * *

UNITED STATES PATENT AND TRADEMARK OFFICE
CERTIFICATE OF CORRECTION

PATENT NO. : 12,036,063 B2
APPLICATION NO. : 16/944666
DATED : July 16, 2024
INVENTOR(S) : Bjurbo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 482 days.

Signed and Sealed this
Thirteenth Day of May, 2025

Coke Morgan Stewart
*Acting Director of the United States Patent and Trademark Office*